(12) United States Patent
Laughlin

(10) Patent No.: US 9,151,716 B1
(45) Date of Patent: Oct. 6, 2015

(54) PORTABLE CARBON MONOXIDE TEST DEVICE FOR SCUBA AIR TANKS

(71) Applicant: Robert M. Laughlin, Miramar, FL (US)

(72) Inventor: Robert M. Laughlin, Miramar, FL (US)

(*) Notice: Subject to any disclaimer, the term of this patent is extended or adjusted under 35 U.S.C. 154(b) by 0 days.

(21) Appl. No.: 13/650,636

(22) Filed: Oct. 12, 2012

Related U.S. Application Data

(60) Provisional application No. 61/546,178, filed on Oct. 12, 2011.

(51) Int. Cl.
| | |
|---|---|
| *G01N 31/22* | (2006.01) |
| *G01N 31/00* | (2006.01) |
| *G01N 33/52* | (2006.01) |
| *G01N 21/77* | (2006.01) |
| *G01N 21/78* | (2006.01) |
| G01N 33/497 | (2006.01) |
| G01N 1/22 | (2006.01) |
| G01N 33/00 | (2006.01) |

(52) U.S. Cl.
CPC .............. *G01N 21/783* (2013.01); *G01N 21/77* (2013.01); *G01N 21/78* (2013.01); *G01N 31/223* (2013.01); *G01N 31/224* (2013.01); *G01N 1/22* (2013.01); *G01N 1/2226* (2013.01); *G01N 33/004* (2013.01); *G01N 33/497* (2013.01); *G01N 2001/2238* (2013.01); *Y10T 436/205831* (2015.01)

(58) Field of Classification Search
USPC ...................... 422/401, 80, 83, 86, 88–89, 94
See application file for complete search history.

(56) References Cited

U.S. PATENT DOCUMENTS

| | | | | |
|---|---|---|---|---|
| 4,256,694 | A | * | 3/1981 | McAllister et al. ........... 422/416 |
| 5,417,204 | A | * | 5/1995 | Moesle, Jr. ............... 128/205.23 |
| 5,439,648 | A | * | 8/1995 | Balderson et al. .............. 422/86 |
| 5,571,948 | A | * | 11/1996 | Kaplan et al. ................ 73/31.05 |
| 5,834,626 | A | * | 11/1998 | De Castro et al. ............. 73/23.3 |
| 6,428,748 | B1 | * | 8/2002 | Wallach ........................ 422/421 |
| 6,468,477 | B1 | * | 10/2002 | Hamilton et al. ............... 422/84 |
| 6,584,826 | B2 | * | 7/2003 | Stephenson et al. ......... 73/31.03 |
| 2002/0029607 | A1 | * | 3/2002 | Stephenson et al. .......... 73/1.01 |
| 2004/0079419 | A1 | * | 4/2004 | Taylor et al. .................. 137/550 |
| 2012/0123287 | A1 | * | 5/2012 | Gedeon ........................ 600/532 |

FOREIGN PATENT DOCUMENTS

EP          1149557 A2 * 10/2001  ............. A61B 5/097

* cited by examiner

*Primary Examiner* — Jennifer Wecker
(74) *Attorney, Agent, or Firm* — Malin Haley DiMaggio & Bowen, P.A.

(57) ABSTRACT

A device for testing a scuba tank air supply for carbon monoxide comprising a transparent or clear inflatable enclosure such as a balloon and a tablet that changes color when exposed to carbon monoxide mounted inside said balloon and a hermetically sealed package containing the balloon and the CO tablet to prevent the activation of the tablet prior to testing the air supply in the scuba tank.

2 Claims, 2 Drawing Sheets

PORTABLE CARBON MONOXIDE TEST DEVICE FOR SCUBA AIR TANKS

BACKGROUND OF THE INVENTION

1. Field of the Invention

This invention relates generally to test equipment to determine if an air supply contains deadly carbon monoxide and specifically to a portable low-cost carbon monoxide test device for use with a SCUBA air tank.

2. Description of the Prior Art

Self-contained underwater breathing apparatus, commonly known as SCUBA, allows a person to swim underwater using a tank of compressed air for breathing. It is critical that the compressed air tank filled with safe air that is not harmful to a human being. In the United States of America typically businesses that provide compressed air periodically are checked for the safety of the air being provided. Such supervision is often not available outside the United States.

In order to ensure that a compressed air tank does not contain carbon monoxide from a bad air compressor, the invention described herein allows a user to quickly determine if the tank's actual air is contaminated with CO gas.

SUMMARY OF THE INVENTION

A device for testing a scuba tank air supply for carbon monoxide comprising a transparent or clear inflatable enclosure such as a balloon and a tablet that changes color when exposed to carbon monoxide mounted inside said balloon and a hermetically sealed package containing the balloon and the CO tablet to prevent the activation of the tablet prior to testing the air supply in the scuba tank.

In order to use the device the user would remove the balloon containing the CO sensing tablet from the airtight package. The open end of the balloon would be attached to the air supply conduit on the scuba tank and the air valve opened, releasing tank air into the balloon which is expanded and filled completely. Once filled, the open end of the balloon is tied into a knot to prevent air from escaping from the balloon. After a set time period, such as ten minutes, the user can observe the CO tablet inside the balloon. If the tablet changes color, then the air supply in the balloon and the tank has carbon monoxide and should not be used.

DESCRIPTION OF THE PREFERRED EMBODIMENTS

Figure 1:
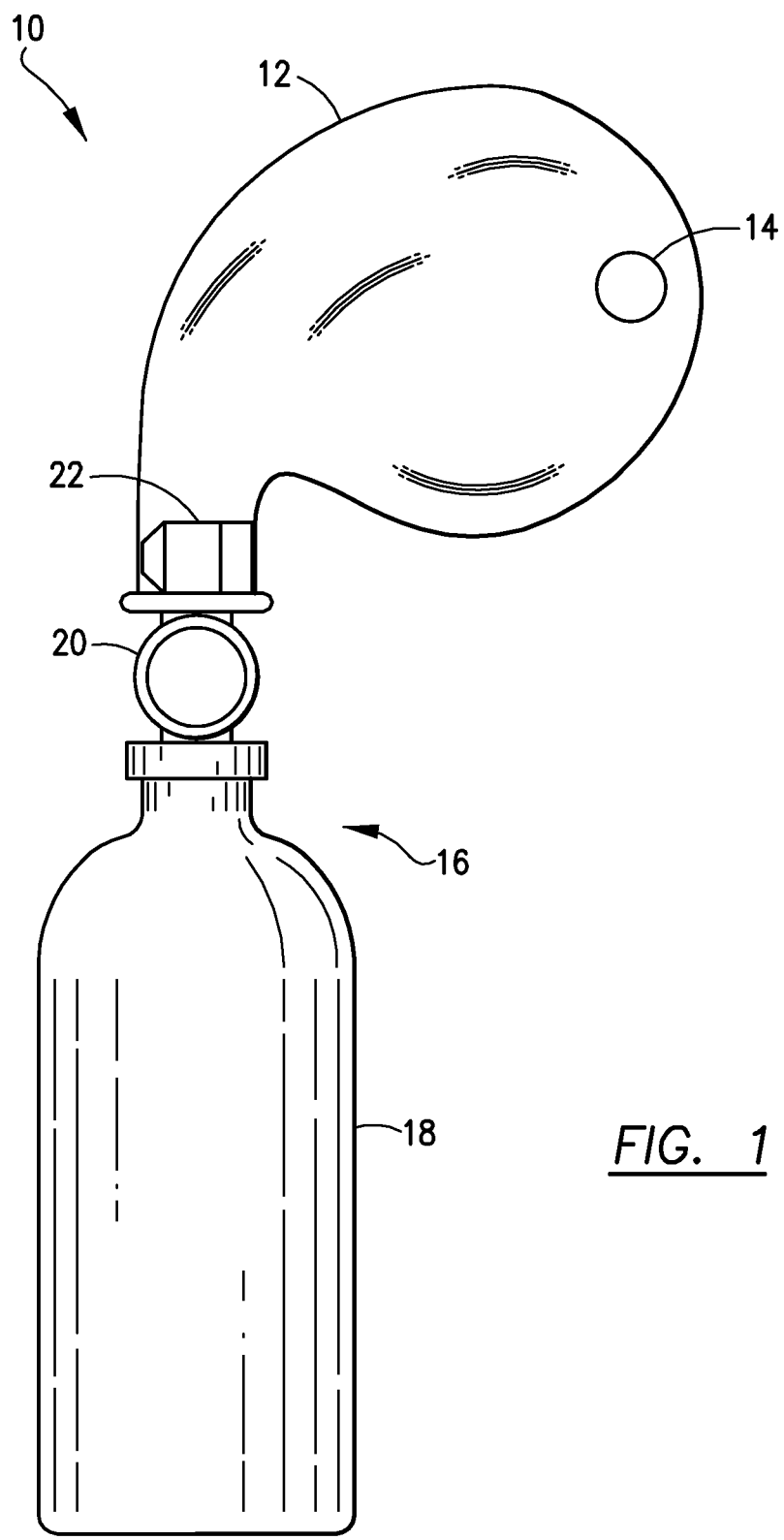
FIG. 1 shows a schematic diagram of a balloon, a CO detecting tablet in said balloon and a scuba tank.

Referring now to the drawing FIG. 1 the present invention 10 is shown comprised of a clear or translucent balloon 12, a CO sensing tablet 14 and a SCUBA tank 16. In order to test the air in the scuba tank 16, the open end of the balloon is placed over the air outlet 22 from the tank 18 and the valve 20 is turned on allowing tank air to escape into the balloon 12 containing a CO sensing tablet 14 that will change color in the presence of carbon monoxide. Once the balloon 12 is filled with tank air, the open end of the balloon 12 is tied into a knot to seal the balloon 12. After a predetermined time such as 10 minutes the user can observe visually the CO sensing tablet 14. If there is no color change the air in the balloon 12 does not contain carbon monoxide. However if the tablet 14 changes color that would indicate that the air supply taken from the tank 18 and put into the balloon 12 contains carbon monoxide.

Figure 2:
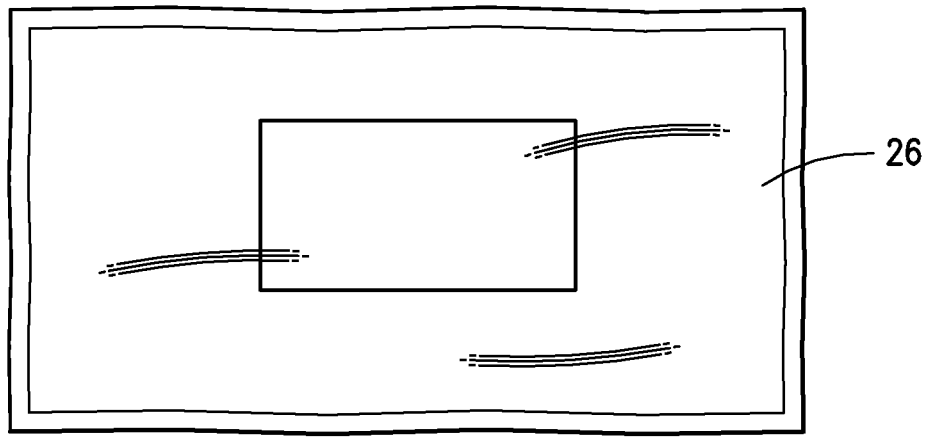
FIG. 2 shows a package for containing the balloons and tablet that is air tight.
Figure 2:
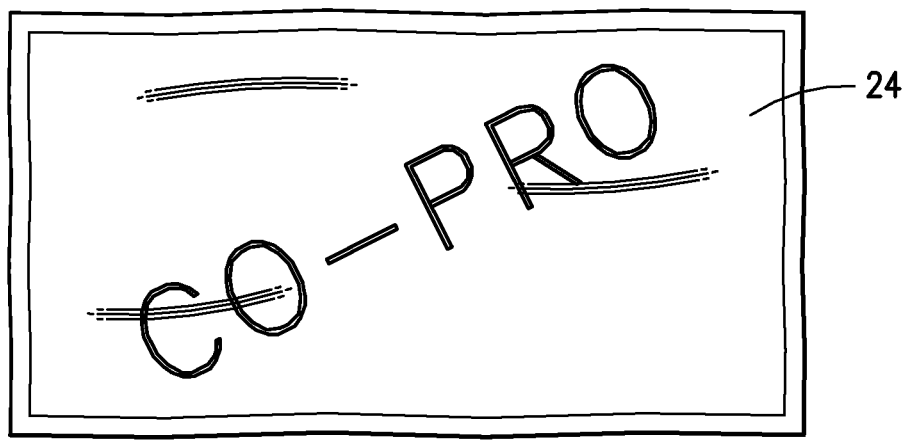

It is important that the balloon 12 and the CO sensing tablet 14 are enclosed in an airtight container 24 (one side) and 26 (other side) prior to use to protect the tablet as shown in drawing FIG. 2.

Thus the invention provides a safe portable low-cost device for testing the air in a scuba tank to determine if carbon monoxide is present.

The instant invention has been shown and described herein in what is considered to be the most practical and preferred embodiments. It is recognized, however, that departures may be made therefrom within the scope of the invention and that obvious modifications will occur to a person skilled in the art.

The invention claimed is:

1. A device for testing a scuba tank having an air supply for carbon monoxide, comprising:
   scuba tank having an air supply for diving, said scuba tank having an air outlet and an air release valve;
   an inflatable balloon made of a transparent material for viewing inside said balloon, said balloon having an open end whose diameter is sized to fit sealably over said tank air outlet;
   said balloon open end being configured to be attached to said tank air outlet;
   a tablet that changes color when exposed to carbon monoxide;
   said tablet mounted inside said balloon and visible through said balloon; and
   wherein said tablet is configured to change color in the presence of carbon monoxide;
   said balloon open end configured to be attached over said scuba tank air supply air outlet for testing for the presence of carbon monoxide in said air supply;
   said balloon configured to be removed from said air supply air outlet and sealed, said tablet inside the balloon configured for testing the air trapped in said balloon,
   wherein said device is configured to be portable.

2. A device as in claim 1, mounted in a sealed package including:
   a hermetically sealed package containing said inflatable balloon and said tablet that changes color when exposed to carbon monoxide inside said balloon to prevent activation prior to testing said air supply in said scuba tanks.

* * * * *